United States Patent [19]

Barrett et al.

[11] Patent Number: 4,595,014
[45] Date of Patent: Jun. 17, 1986

[54] IMAGING PROBE AND METHOD

[75] Inventors: Harrison H. Barrett; Herbert B. Barber; Walter J. Wild, all of Tucson, Ariz.

[73] Assignee: University Patents, Inc., Westport, Conn.

[21] Appl. No.: 542,953

[22] Filed: Oct. 18, 1983

[51] Int. Cl.⁴ .............................................. A61B 6/00
[52] U.S. Cl. ............................... 128/654; 250/363 S; 378/2; 378/149; 128/659
[58] Field of Search ....................... 128/653, 654, 659; 250/363 SD, 363 SR, 368, 370 GX; 378/2, 149, 150

[56] References Cited

U.S. PATENT DOCUMENTS

| | | | |
|---|---|---|---|
| 3,413,466 | 11/1968 | Allen, Jr. ............................ | 250/368 |
| 3,670,719 | 6/1972 | Kobayashi et al. .................. | 128/659 |
| 3,752,982 | 8/1973 | Jaszczak ............................ | 250/368 |
| 3,916,198 | 10/1975 | Coltman et al. ................... | 250/363 SD |
| 4,015,592 | 4/1977 | Bradley-Moore .................... | 128/659 |
| 4,165,462 | 8/1979 | Macovski et al. .................. | 250/363 S |
| 4,197,836 | 4/1980 | Wagner et al. .................... | 250/363 S |
| 4,209,780 | 6/1980 | Fenimore et al. ............... | 250/363 SD |
| 4,262,207 | 4/1981 | Tosswill . | |
| 4,389,633 | 6/1983 | Fenimore ....................... | 250/363 SD |

FOREIGN PATENT DOCUMENTS

| | | | |
|---|---|---|---|
| 2072839 | 10/1981 | United Kingdom ......... | 250/363 SD |
| 560195 | 6/1977 | U.S.S.R. ....................... | 250/363 SD |

OTHER PUBLICATIONS

Cannon et al., "Coded Aperture Imaging: Many Holes Make Light Work" *Optical Engineering* May/Jun. 1980, vol. 19, No. 3, pp. 283-289.

Akcasu et al., "Coded Aperture Gamma Ray Imaging With Stochastic Apertures", Conference: *Application of Optical Instrumentation in Medicine* 2nd Seminar Chicago Ill., Nov. 29-30, 1973, pp. 17-28.

Dowdey et al., "Coded Apertures for Nuclear Medicine Imaging", *Applied Radiology*, Jul.-Aug. 1977, pp. 145-151, 168-169.

*Primary Examiner*—Kyle L. Howell
*Assistant Examiner*—Ruth S. Smith
*Attorney, Agent, or Firm*—Martin Novack

[57] ABSTRACT

The disclosure is directed to an apparatus and method for imaging radiation pattern from within a body. In accordance with the preferred method of the invention, there is provided a technique for imaging internal structure of a body which includes the following steps: a radiation-emitting substance is introduced into the body. A miniaturized probe is inserted into the body, the probe being coupled to a cable and including at least one radiation detector surrounded by a coded aperture. Signals are received from the detector via the cable for a series of positions of the probe and for different orientations of the coded aperture with respect to the body. The signals from the detector are processed to obtain an image of the radiation pattern within the body. The imaging hereof allows both the position and the strength of a source (e.g. a tumor) to be determined in the presence of background radiation. The use of an internal probe simultaneously allows advantage to be taken of the increase in count rate and resolution resulting from proximity to the source.

17 Claims, 13 Drawing Figures

IMAGING PROBE AND METHOD

This invention was made in the course of work supported by the National Cancer Institutes, grant 2 PO1 CA 23417.

BACKGROUND OF THE INVENTION

This invention relates to imaging of radiation from within an animate or inanimate body using a probe that is insertable into the body.

In nuclear medicine, a commonly used technique for cancer detection involves injecting a radioisotope-labeled pharmaceutical which localizes preferentially in tumors. The location and extent of tumor can then be assessed by imaging the gamma ray emissions of the radioisotope using a gamma camera. Because of the limited spatial resolution and efficiency of existing gamma cameras as well as such considerations as patient dose and specificity of the tumor-seeking radiopharmaceutical, it has proved difficult in practice to image tumors smaller than one or two centimeters in size. Since early detection may be important for patient survival, it is important to detect the smallest possible tumors.

It is known that the sensitivity, resolution, and/or signal-to-noise ratio of detectors and gamma cameras can be increased using coded-aperture techniques. Uniformly redundant arrays and other coded apertures have been successfully employed to obtain images of radiation sources, with enhanced sensitivity, resolution, and/or signal-to-noise ratio. See, for example; R. G. Simpson and H. H. Barrett, "Coded-Aperture Imaging" (In "Imaging in Diagnostic Medicine"), p.p. 217–311. Plenum, New York, H. H. Barrett, "Fresnel Zone Plate Imaging in Nuclear Medicine", J. Nucl. Med. 13, 382 (1972); H. H. Barrett and F. A. Harrigan, "Fresnel Zone Plate Imaging of Gamma Rays; Theory". Applied Optics, 12 2686 (1973); U.S. Pat. Nos. 4,165,462, 4,209,780, and 4,262,207.

Small radiation detectors have been developed which can be inserted into the body in the immediate vicinity of the tumor, for example, during bronchoscopy or surgery. See, for example, H. B. Barber, et al., "Miniature Radiation Detectors for Surgical Tumor Staging", 32 ACEMB, Denver, Colo., 6–10 October 1979; H. B. Barber, et al., "Small Radiation Detectors for Bronchoscopic Tumor Localization", IEEE Transactions on Nuclear Science, Vol. NS-27, No. 1, February 1980. Such detectors have the advantage of increased count rate due to proximity to the source. A disadvantage of such detectors is that they are sensitive to radiation from all directions so that the unavoidable uptake of the radiopharmaceutical in normal tissue constitutes a significant background source. Any local nonuniformity of such uptake exacerbates the problem and makes the detection of small tumors more difficult.

It is an object of the invention to provide an improved system and method for obtaining information about radiation in a body.

SUMMARY OF THE INVENTION

The present invention is directed to an apparatus and method for imaging a radiation pattern from within a body.

In accordance with the preferred method of the invention, there is provided a technique for imaging internal structure of a body which includes the following steps: a radiation-emitting substance is introduced into the body. A miniaturized probe is inserted into the body, the probe being coupled to a cable and including at least one radiation detector surrounded by a coded aperture. As used herein, the term "coded aperture" is intended to mean any pattern of one or more radiation-transparent openings in a radiation-opaque body, including but not limited to: pinhole analogs, uniformly redundant array codes and other codes, and Fresnel zone plates. Signals are received from the detector via the cable for a series of positions of the probe and for different orientations of the coded aperture with respect to the body. The signals from the detector are processed to obtain an image of the radiation pattern within the body.

The imaging hereof allows both the position and the strength of the source (e.g. a tumor) to be determined in the presence of the background radiation. The use of an internal probe simultaneously allows advantage to be taken of the increase in count rate and resolution resulting from proximity to the source.

In accordance with the apparatus of the invention, a cable is provided, and a miniaturized probe is coupled to the cable and is insertable into the body, as previously indicated. The probe, which includes at least one radiation detector, has a plurality of axial collimators disposed around said at least one detector. A coded aperture azimuthal collimator is also disposed around said at least one detector, preferably outside the axial collimators. Means are provided for obtaining output signals from the at least one detector for a series of rotational orientations of the azimuthal collimator, and for a series of positional translations of the probe, the outputs being carried by the cable. Means outside the body are provided, responsive to the output signals received via the cable, for processing the output signals to obtain an image.

In one embodiment hereof, the means for obtaining output signals from said at least one detector comprises means for rotating the azimuthal collimator on its axis and obtaining detector outputs at different rotational orientations of the azimuthal collimator. In this embodiment, the coded aperture azimuthal collimator comprises a cylinder formed of a radiation-opaque material having radiation-transparent apertures therein. The apertures are formed in a pattern of a uniformly redundant array binary code. The means for processing the output signals to obtain an image is operative to correlate the output signals with the coded aperture pattern.

In another embodiment of the invention, the at least one radiation detector comprises a plurality of individual detectors. In this embodiment, the coded aperture azimuthal collimator includes a plurality of collimator rings, one for each detector. The collimator rings each have the same coded aperture pattern thereon, the coded aperture patterns of the rings being at different relative rotational positions.

Further features and advantages of the invention will become more readily apparent from the following detailed description when taken in conjunction with the accompanying drawings.

DESCRIPTION OF THE PREFERRED EMBODIMENTS

Figure 1:
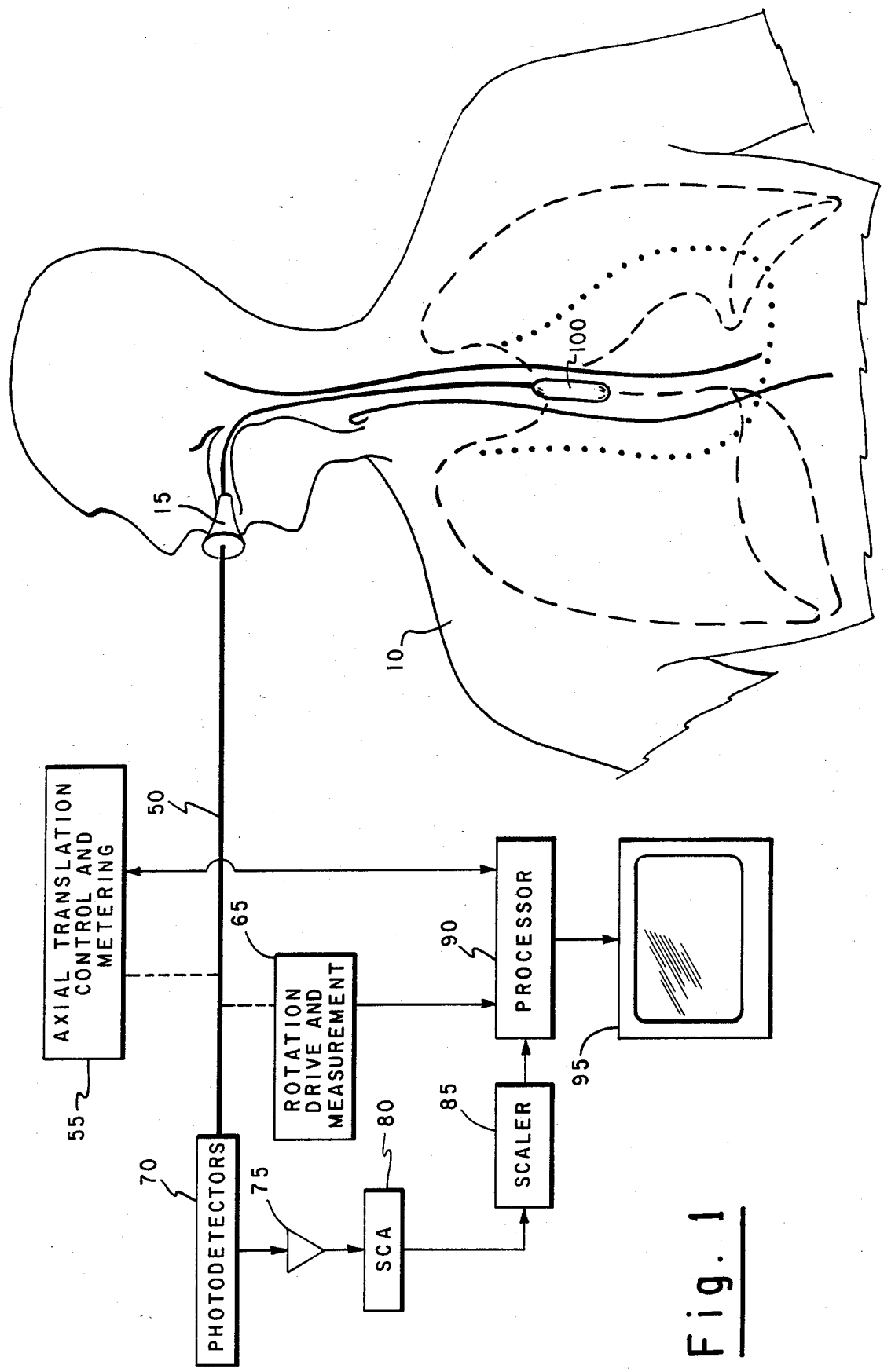
FIG. 1 is a diagram, partially in block form, illustrating the use of the invented apparatus and method.

Referring to FIG. 1 there is shown an example of an apparatus in accordance with the invention being used for imaging from within a human body 10 into which a radioactive tracer had been injected. An imaging probe 100, to be described further hereinbelow, is disposed at the end of a cable 50 that is used to position and move the probe and, in the illustrated embodiments hereof, also to convey power and data to and from the probe 100. In the pictured example, the cable 50 is under control of a metering device 55 used to keep track of the length of cable, so that the extent of probe insertion into the body can be measured. The metering device 55 may be of any known type, such as one wherein the length of cable is calibrated using optically read marks. Alternatively, the extension of the probe can be determined by other means, such as by reading the position of reference marks on a mouthpiece 15. In the illustration, the cable and probe are shown as extending into the esophagus. For safety's sake, measurements are preferably made during removal, rather than insertion, of the probe from the body under manual control.

In the embodiments hereof, the probe 100 includes one or more radiation detectors which may comprise, for example, scintillation crystals coupled to photomultiplier tubes. In one embodiment, to be described, a single scintillation detector is coupled to a fiber optic light guide in cable 50, and a photodetector, such as a photomultiplier tube or photodiode, is located at the other end of the fiber optic light guide, as represented by photodetector block 70 in FIG. 1. In this embodiment the probe has a rotatable azimuthal collimator, the control and monitoring of rotation being represented by block 65. In another embodiment, wherein multiple radiation detectors are employed, and no rotation is necessary, each radiation detector can have an associated fiber optic light guide in the cable 50, in which case photodetector block 70 would include a photodetector associated with each fiber optic guide. The photodetectors(s) may also be located within the probe itself. Alternatively, if the detector(s) in the probe are of a type which converts the radiation to be detected into an electronic signal, as described herein in conjunction with one embodiment, a conductor can be provided for each detector, or a suitable multiplexing scheme can be employed. Accordingly, the photodetector block may be unnecessary.

Electronic signals representative of the outputs of the one or more radiation detectors in the probe 100 are coupled via amplifier(s) 75, single channel analyzer 80 and digital scaler 85, to digital processor 90. The single channel analyzer, which may be of the type made by Canberra Instruments, operates to select events with energies in the region of the gamma radiation line chosen, this being done to reject background events which result from Compton scattering. The processor 90, which may be any suitable computer or microprocessor, conventionally has associated memory that can store the raw data from the detector as well as data that is processed as described below. An example of a processor which can be used is the PDP-11 microcomputer sold by Digital Equipment Corp. The processed data is coupled to a video display 95. If a digital processor is employed, suitable analog-to-digital and/or digital-to-analog converters can be provided, as necessary.

In operation, at each axial position of the probe (the axial position being defined, for example, by the depth of insertion of the probe into the body) the azimuthal radiation pattern around the probe is detected, in a manner to be described, and the detector data is either stored for subsequent processing or is processed in real time. Data can then be collected at subsequent axial positions (either continuously or in stepped fashion), and the resultant data can be used to obtain a two dimensional cylindrically mapped image of the distribution of radiation sources around the probe axis.

Figure 2:
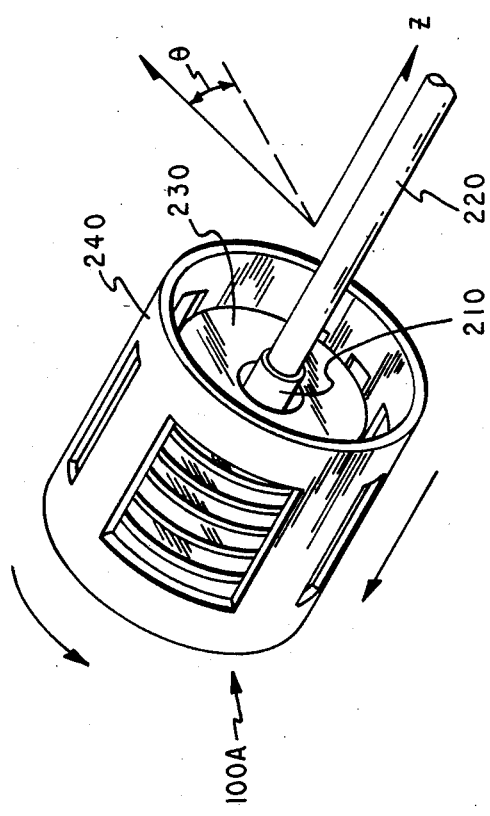
FIG. 2 is a prospective view of a probe in accordance with an embodiment of the invention.
Figure 4:
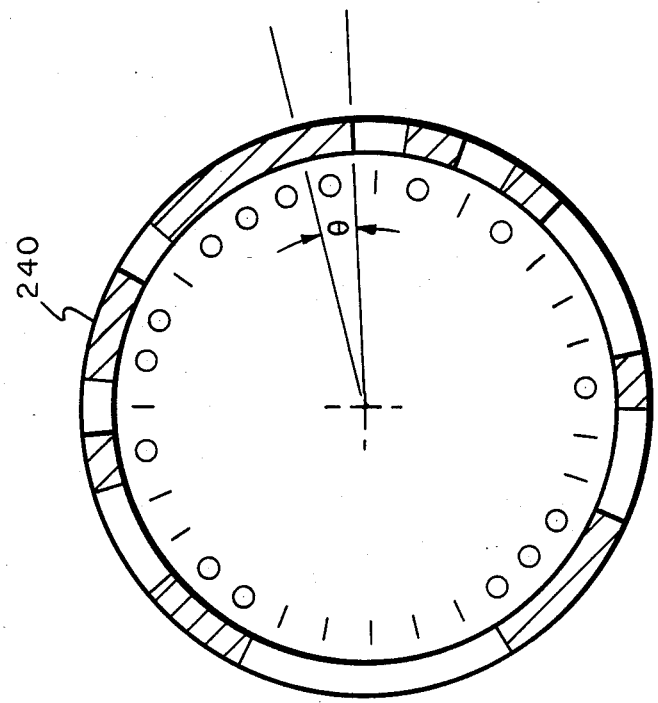
FIG. 4 is a representation of a cross-section through the rotatable collimator of the FIG. 2 embodiment, showing the uniformly redundant array coded aperture pattern thereof.
Figure 3:
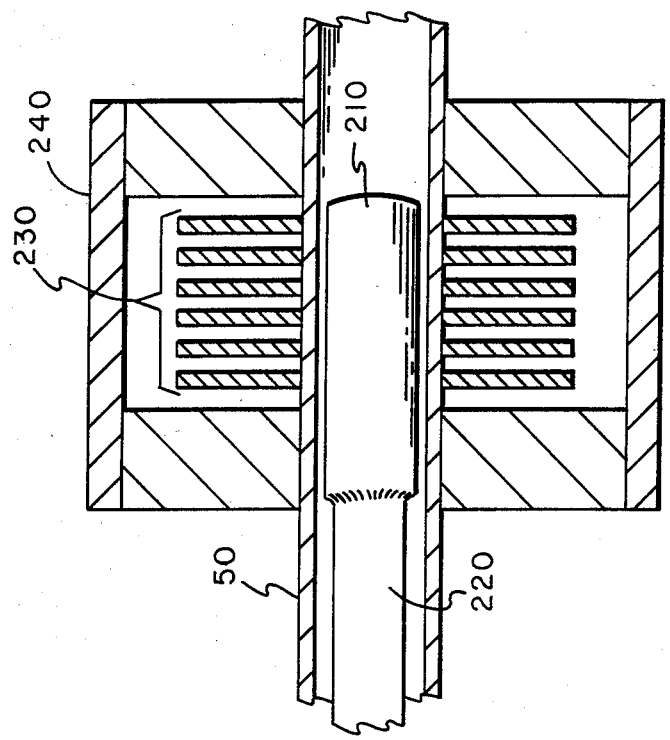
FIG. 3 is a cross-sectional view of the probe of the FIG. 2 embodiment.

Referring to FIGS. 2 and 3, there are shown diagrams of a probe 100A in accordance with one of the embodiments of the invention. In this embodiment, a single radiation detector 210 is employed at the end of a light guide 220 in cable 50. In a form of this embodiment, the detector is a NaI (T1) detector, although it will be understood that in all embodiments hereof alternative types of detectors can be employed, for example a semiconductor detector, or ionization chamber for the detection of x rays, gamma rays, or particulate radiation, depending upon the application. An axial collimator 230 is provided and includes a number of disc-shaped parallel lead sections, there being six shown in the illustration of FIGS. 2 and 3. An azimuthal collimator 240 serves as a coded aperture, and includes a lead cylinder with azimuthally coded slots and lead end caps, (not shown in the FIG. 2 view), mounted over the axial collimator. The azimuthal collimator is rotatable about its axis, and the code function thereof is a uniformly redundant array ("URA"). URAs, and the counting statistics thereof, are described in "Radiological Imaging" by Barrett and Swindell, published by Academic Press, which is incorporated herein by reference. The diagram of FIG. 4 shows a 31 element one-dimensional binary coded URA, with the code 0000100101100111110001101110101 where "0" represents a filled element and "1" is an open element. In this case, each element has an angle of 11.6 degrees.

To understand the operation of this embodiment, the cylindrical coordinate system of FIG. 2 $(r,\theta,z)$ is useful. The z axis coincides with the axis of the lead cylinder 240, and the transmission of the cylinder as a function of θ is the URA code function. An angular coded image, a function of θ, is formed during one rotation of the cylinder. Decoding is carried out by correlating the coded image with a bipolar version of the code function; i.e., with −1's in the place of the 0's in the exemplary code function above. This decoding operation has the effect of converting the code function into a sharply peaked point spread function. The decoded image has an angular resolution of 2 π divided by the number of elements in the URA. The disc collimator provides resolution in the z direction, and image information in this direction is obtained by scanning the probe axially. The final image is thus a function of θ and z; no information about the r direction is obtained.

Figure 5:
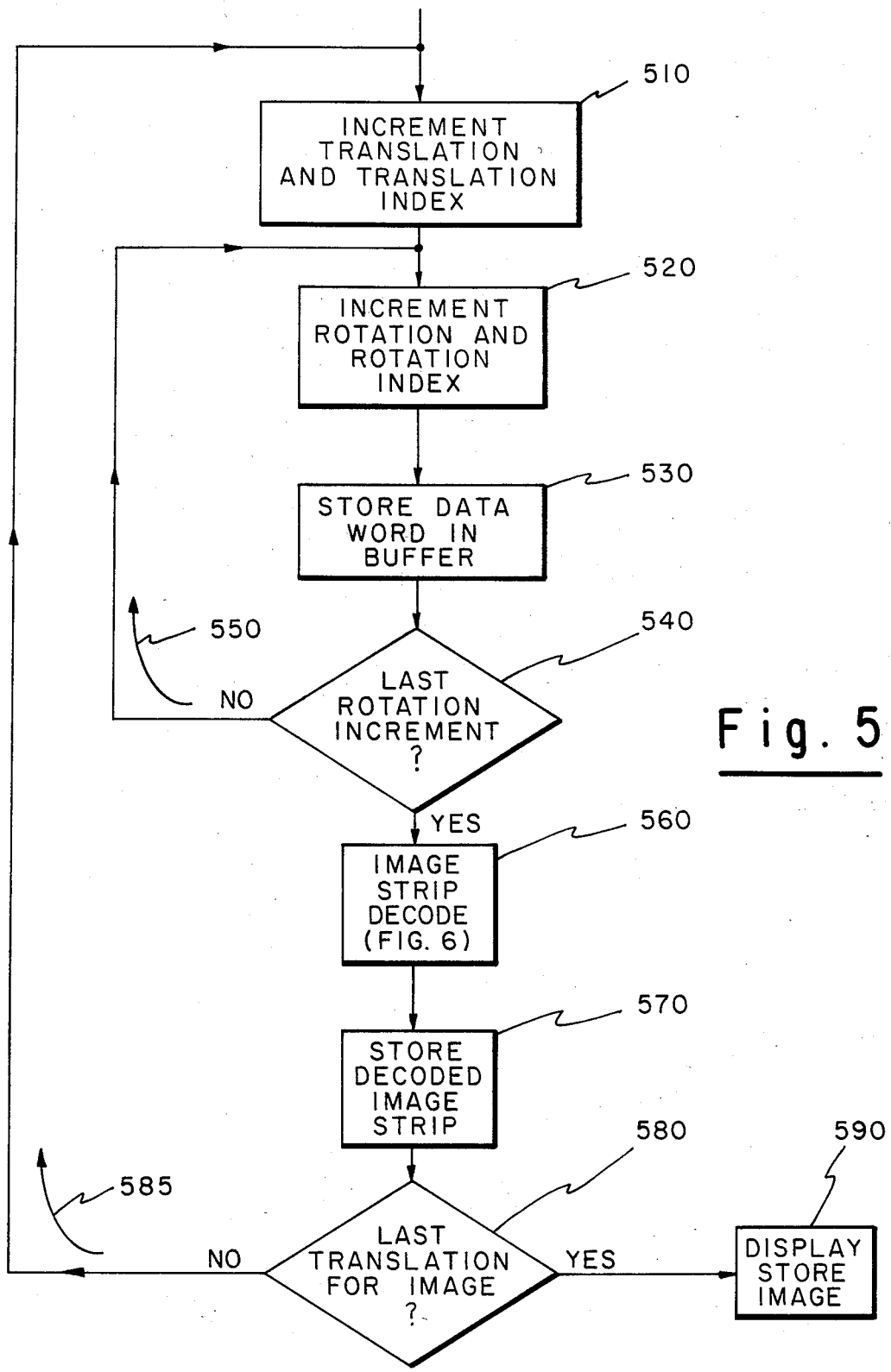
FIG. 5 is a flow diagram of a routine for programming a processor for control of the FIG. 2 embodiment.

Referring to FIG. 5, there is shown a flow diagram of a routine suitable for programming the processor 90 (FIG. 1) for control of the probe of the FIG. 2 embodiment which includes the rotating azimuthal collimator. The block 510 represents the incrementing of translation (either automatically or manually, with manual input to the processor that this has been done), and the incrementing of an associated translation index. The block 520 represents the implementation of a rotation increment (e.g. via rotation drive 65), and the incrementing of a rotation index which is used to keep track of rotational orientation. The digitized data word (from scaler 80, FIG. 1) for this particular rotational increment is then stored (block 530), and inquiry is made (diamond 540) as to whether or not there has been a complete revolution of rotational increments. If not, the block 520 is re-entered, and the loop 550 is continued, with a data word being stored at each rotational increment. After the last rotational increment, the block 560 is entered, this block representing the image strip decoding process whereby the strip of data taken at the particular translation position is decoded to obtain a cylindrical image strip.

Figure 6:
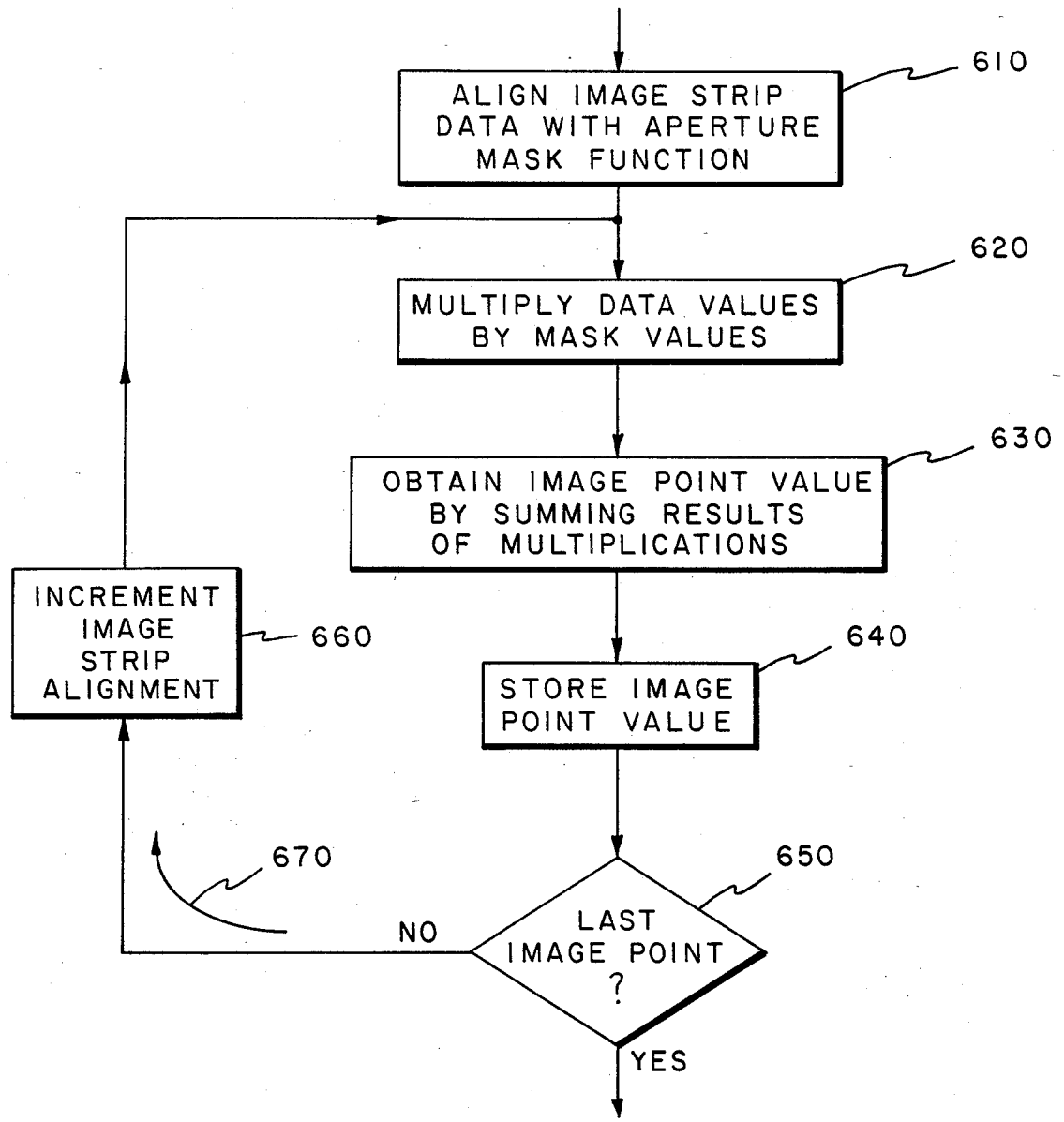
FIG. 6 is a flow diagram of the image strip decoding routine of the FIG. 5 flow diagram.

The routine represented by the block 560 is shown in FIG. 6, to be described. While this routine is illustrated as being performed at a particular time in the routine of FIG. 5, it will be understood that alternatively a processor could routinely coordinate the image strip decoding to be performed either simultaneously with the collection of data, during available shared processor time, or after collection of all data, as desired.

The decoded image strip is stored (block 570), and inquiry is made (diamond 580) as to whether or not it is the last translation for a particular imaging procedure or portion of an imaging procedure. If not, the block 510 is re-entered, and the loop 585 is continued. If so, however, the stored image can be displayed, as represented by the block 590. It will be understood that, if desired, the image can be displayed continuously, as generated, and the raw data can also be presented, if desired.

Referring to FIG. 6, there is shown a flow diagram of the image strip decoding routine represented generally by the block 560 of FIG. 5. The image strip data is initially aligned with an initial position of the aperture mask function, as represented by the block 610. Preferably, a bipolar aperture mask function is used; e.g. with a +1 value for an open elemental position, and a −1 value for a closed (or opaque) elemental position. The data values are then multipled by the mask values, as represented by the block 620. An image point value is next obtained by summing the results of the multiplications (block 630). The image point is stored (block 640), and inquiry is made (diamond 650) as to whether or not the last image point has been processed. If not, the image strip alignment is incremented with respect to the aperture mask function, and the loop 670 continues in this manner until decoded image points have been obtained and stored for the entire image strip. It will be understood that the correlation used for decoding can be performed in various alternative ways including use of matrix multiplications and transforms. In the embodiment hereof, a bipolar mask function is utilized, although other suitable mask functions can be used.

Figure 7:
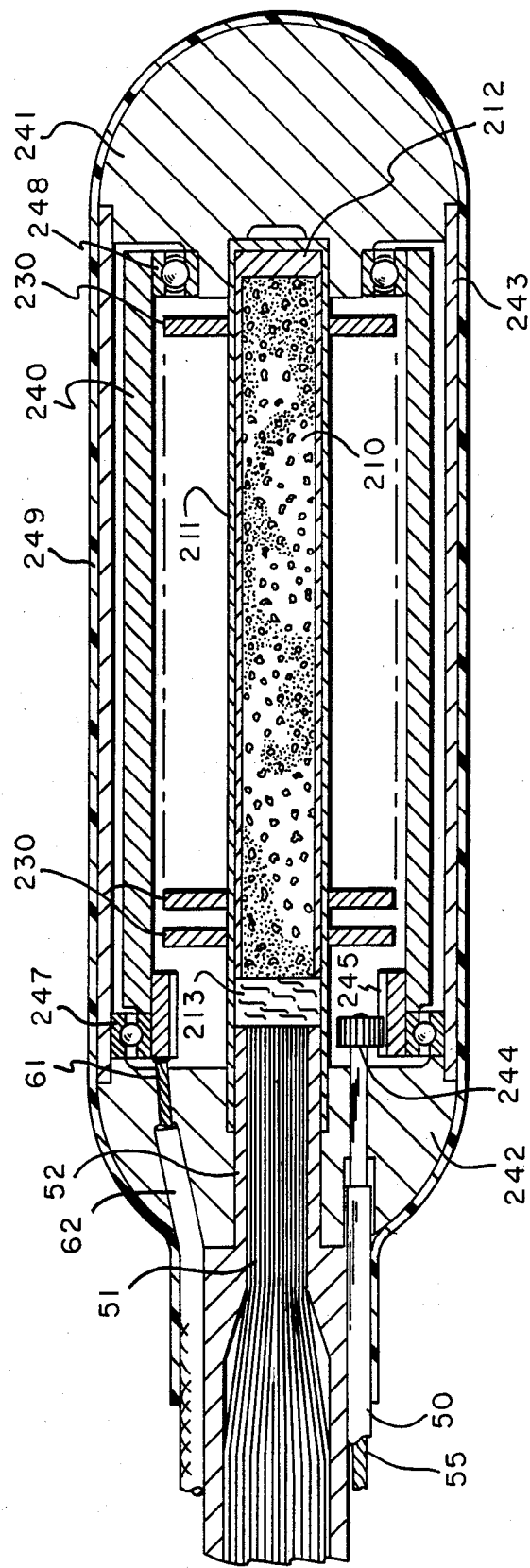
FIG. 7 is a cross-sectional view of a probe in accordance with an embodiment of the invention.

Referring to FIG. 7, there is shown a diagram of the probe 100A of the FIG. 2 embodiment, including further detail of the structure. The NaI(T1) detector 210 is mounted in an aluminum container 211 between fixed lead endcaps 241 and 242 that are connected by an aluminum sleeve 243. A plastic coating 249 covers the entire device. Light is coupled out of the scintillation crystal 210, which is packed in a white reflectance coating 212, by a glass window 213 at the proximal end. Optically coupled to the window 213 is a fiberoptic light guide 51 whose end is mounted in a clamp 52 within cable 50 and an opening in end cap 242. This light guide is coupled to photodetector 70 (FIG. 1). The axial collimator discs 230 are fixedly mounted on the detector container 211. (Alternatively, they could rotate with the azimuthal collimator, in which case the two collimator units could be pictured as a one-piece hollow cylinder with apertures.) The rotating azimuthal collimator 240 is located in the region between the axial collimator and the sleeve 243. The collimator 240 is free to rotate and has gearing 245 machined to its inner surface at the proximal end. A driving gear 244 engages the collimator gearing 245 and is coupled to a torsional cable 55, within cable 50, which carries the desired torque to the drive gearing. The torsional cable is coupled at its other end to rotation drive 65. Bearings 247 and 248 are provided near the rotating collimator ends. A rotation monitor is provided and includes an electrical brush 61 which contacts an edge surface of the rotating collimator. The region of contact on the rotating collimator contains alternating conducting and non-conducting regions. Rotation is monitored by a conductance sensor in rotation measurement and block 65 drive circuit, via wire 62 in cable 50.

Figure 8:
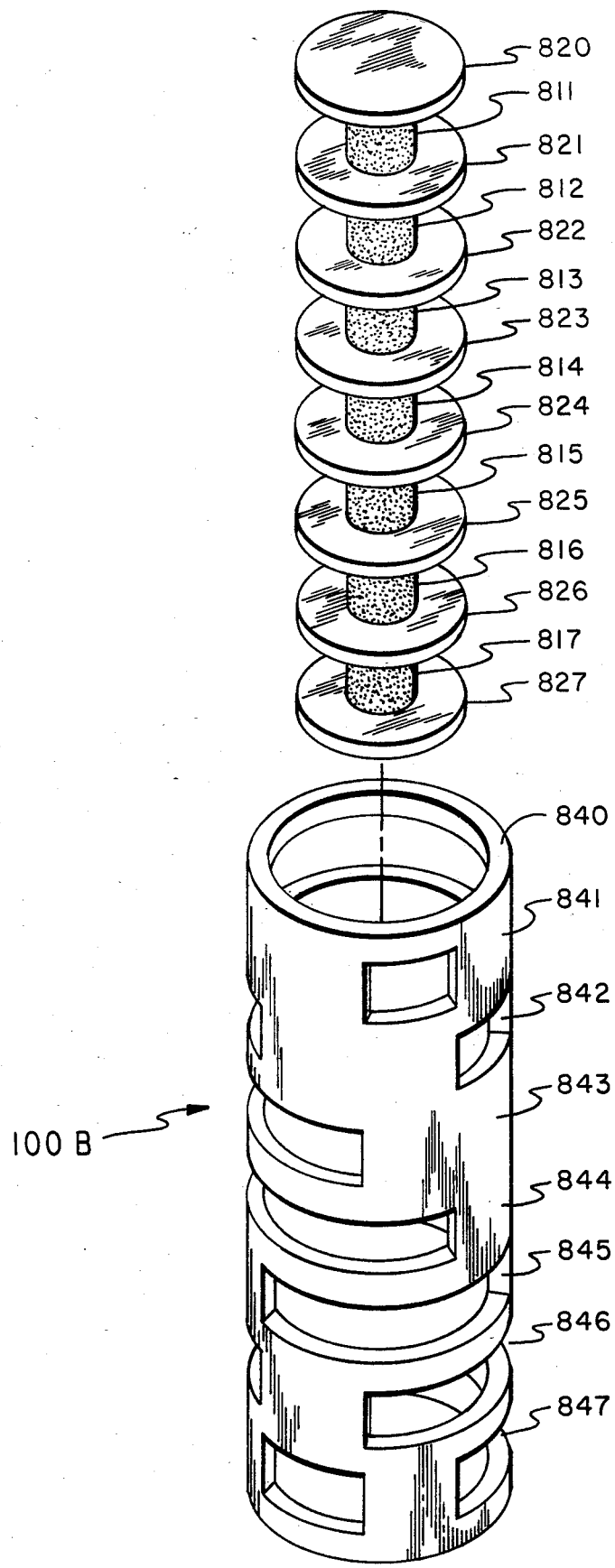
FIG. 8 is an exploded view of a probe in accordance with another embodiment of the invention.
Figure 9:
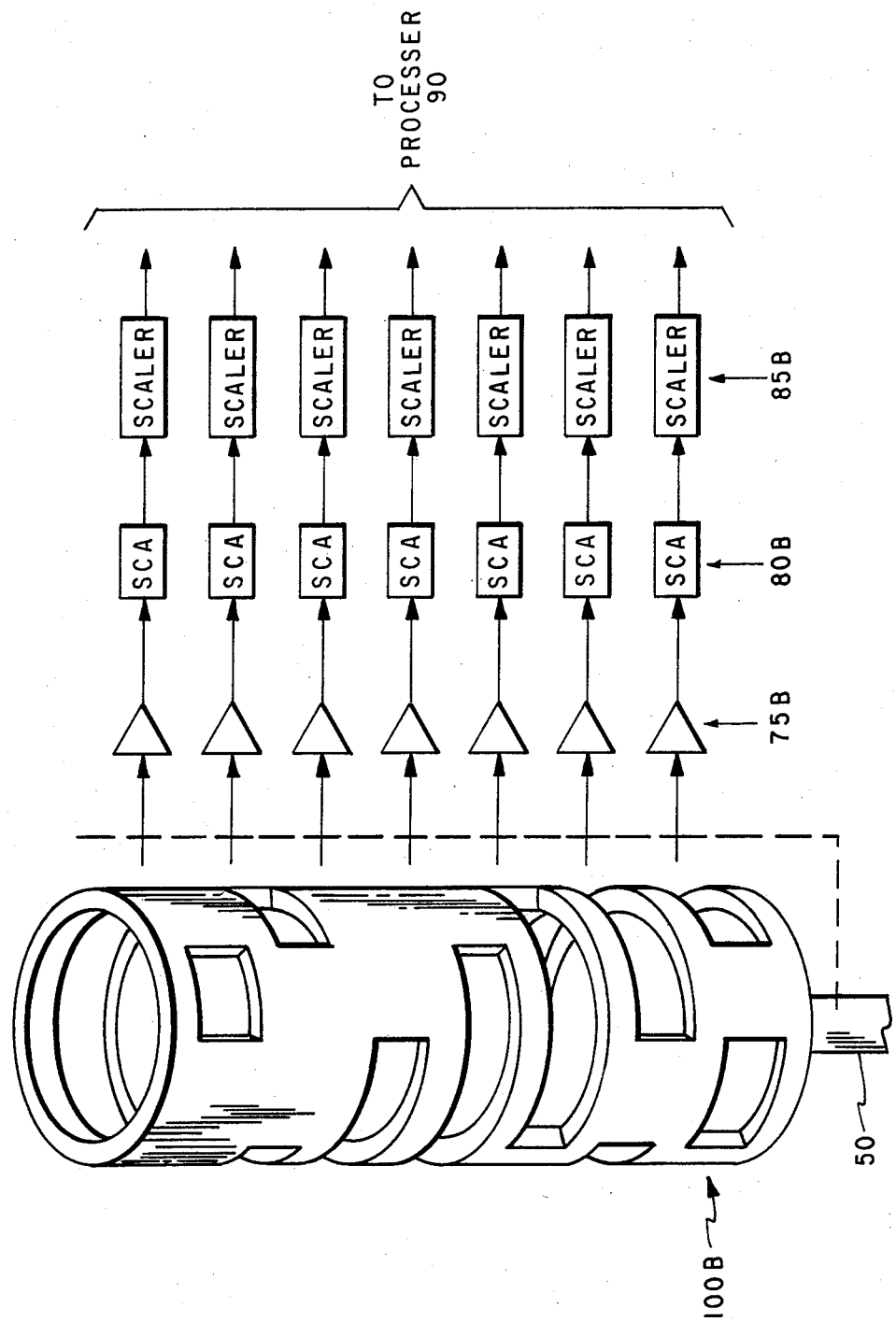
FIG. 9 is a block diagram of a portion of the signal processing of the FIG. 8 embodiment.
Figure 10:
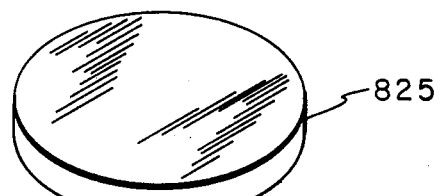
FIG. 10 shows an individual detector and associated collimators of the FIG. 8 embodiment.
Figure 10:
Figure 10:
Figure 10:
Figure 10:
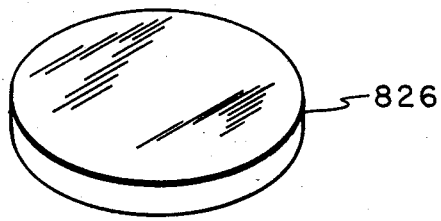

In the embodiment of FIG. 8, shown in exploded view, a number of individual detectors are utilized in probe 100B, there being seven detectors 811–818 shown in the FIGURE for ease of illustration. The lead axial collimators 820–828 are disc shaped and separate the detectors, the collimator elements 820 and 828 serving as end caps, as well. In this embodiment the detectors 811–817 are room temperature semiconductor CdTe detectors which are coupled electrically through cable 50 to respective amplifiers 75B, SCAs 80B, and scalers 85B, to processor 90, as shown in FIG. 9. FIG. 10 shows an exemplary one of the detectors, 816, separated from its adjacent collimator discs 825 and 826, by insulator discs 835 and 836. The leads from the detector can be coupled through small openings (not shown) in the axial collimator discs.

Figure 11:
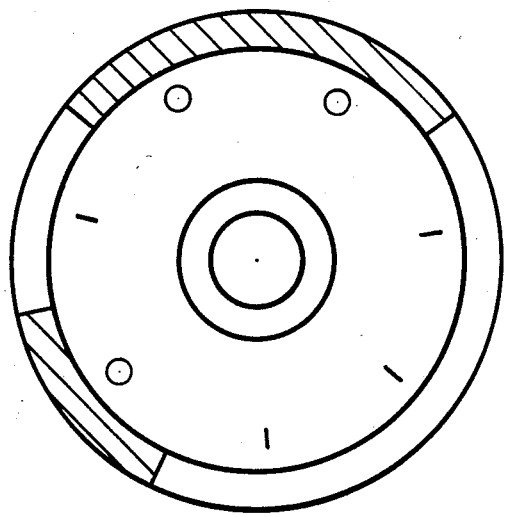
FIG. 11 is a cross section through one of the azimuthal collimator rings of the FIG. 8 embodiment, showing the uniformly redundant array coded aperture pattern thereof.

A cylindrical azimuthal collimator 840 is provided in this embodiment, and includes a series of collimator rings 841–847, each of which has a uniformly redundant array coded aperture in the same pattern, but with adjacent rings having the array displaced rotationally by one element. If the number of detectors provided is the same as the number of elements in the uniformly redundant array (for example, in the illustration there are seven detectors and seven elemental orientations of the uniformly redundant array—see FIG. 11 which shows the URA pattern 0100111), the various detectors and their associated azimuthal ring-shaped collimator sections can be thought of as a single detector having an associated uniformly redundant array collimator which has been rotated to a series of different orientations during one full rotation. That is, each detector "sees" an azimuthal uniformly redundant array that is rotated one element in sequence with respect to what is seen by the adjacent detector. In this manner, the probe 100B codes angular information in the separate response of each detector without the need for rotation.

If a source being viewed is sufficiently distant from the detector array that it is equally well viewed by each dector simultaneously, then at a given probe position the outputs of all detectors would provide information about the source as taken from each rotational orientation. On the other hand, if the source is small and very close to the detector it may be only within the field of view of a single detector at any given time. However, axial translation in this system, as in the previous embodiment, provides one dimension of the image with axial collimation providing the resolution in that dimension. If data is taken continuously with axial motion it is clear that each detector will eventually, and in turn, view the source after a delay that depends on the axial position of the detector, and with a duration corresponding to the distance of the source from the detector. As further described below, the stored record of the temporal response of each detector can then be appropriately binned and the expected delay removed to obtain a coded pattern which can be correlated with the aperture function to yield an image in a manner similar to that of the FIG. 2 embodiment. This procedure provides enhancement of the image for a cylindrical region about the probe axis. If desired, a similar procedure can be implemented with respect to the FIG. 2 embodiment, as well.

Figure 12:
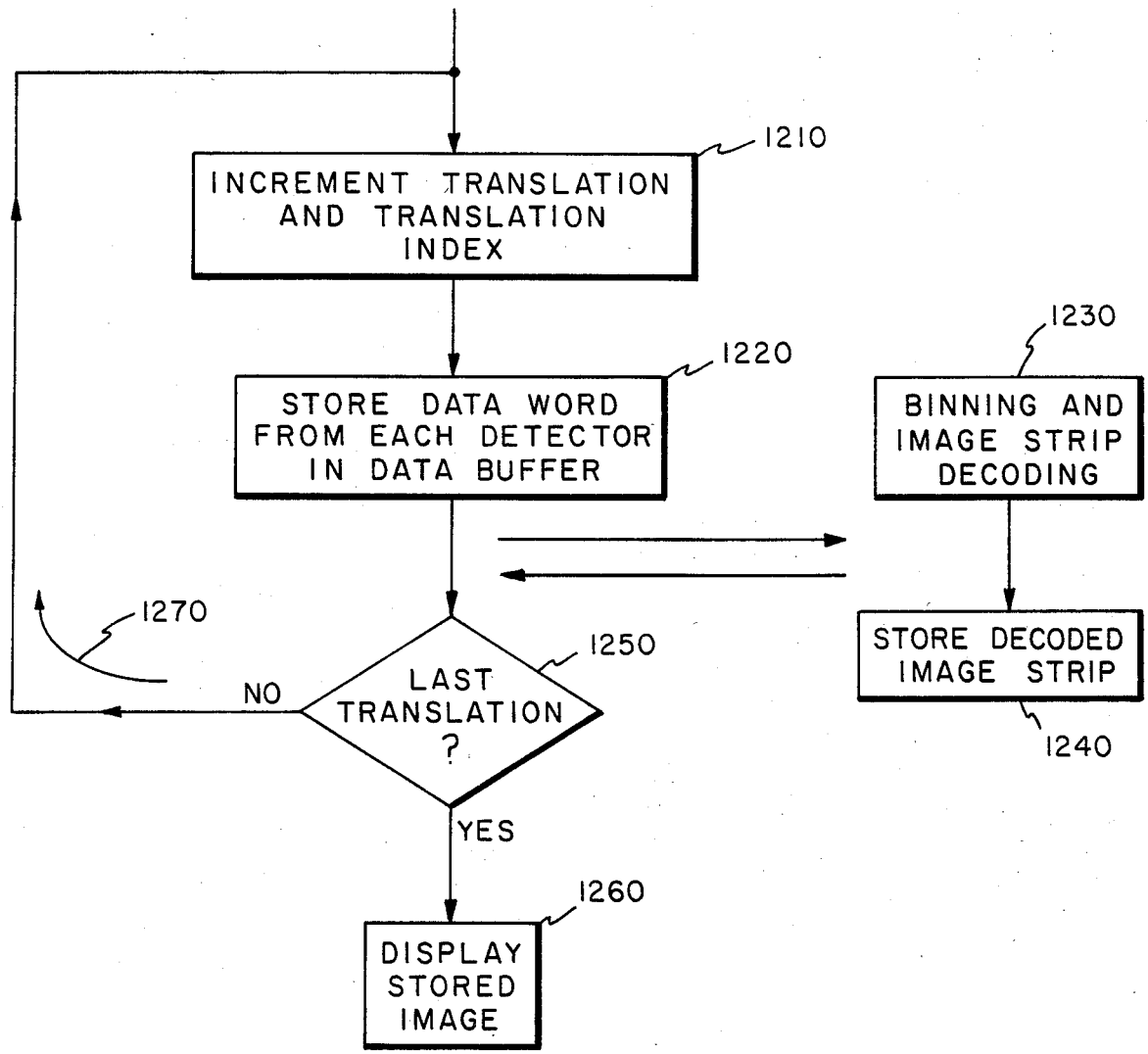
FIG. 12 is a flow diagram of a routine for control of the processor of the FIG. 8 embodiment.

Referring to FIG. 12, there is shown a flow diagram of a routine suitable for programming the processor for use in conjunction with the non-rotating probe 100B of the FIG. 8 embodiment. The block 1210 represents the translation incrementing and indexing, which may be implemented in a manner similar to that previously described. In the present embodiment, however, translation increments can, if desired, be smaller than in the previous embodiment; i.e., translation by a distance equal to the axial collimator spacing, so that the probe is moved by one detector length rather than, for example, a full probe length (as in the rotating embodiment) at each translation increment. The data word from each detector 811-817 is then stored in a data buffer, as represented by block 1220. Image strip decoding (and binning, to be described) can then be implemented, as represented by block 1230, and described in conjunction with the flow diagram of FIG. 13. A decoded image strip can then be stored, as represented by the block 1240. As previously noted, the image strip processing can be performed in various orders in the sequence, or after all data has been stored. Inquiry is then made (diamond 1250) as to whether or not the last translation of a particular procedure or portion of a procedure has been implemented. If not, the block 1210 is re-entered, and the loop 1270 is continued. The block 1260 represents the display of the stored image which, again, can be implemented upon completion of the decoded image, or at any time during processing.

Consistent with the previous description, the non-rotating embodiment of FIG. 8 can be initially understood in terms of its use in a set-up wherein the probe translation increments are the same as in the rotating embodiment; i.e., for example, translation by the length of the full detector array). Since each annular section of the non-rotating azimuthal collimator is equivalent to a different rotational orientation of the rotating collimator in the FIG. 2 embodiment, it will be understood that the outputs of detectors 811-817 are equivalent, from a relative rotational standpoint, to the outputs taken at different rotational increments of one complete revolution of the FIG. 2 azimuthal collimator.

If, for example, the translation incrementation in the present embodiment is by a distance equal to the distance between individual detector elements, then since each detector is "looking" in substantially the same rotational reference direction during successive translation increments, the data words obtained at each detector output over a series of increments can be combined so as to obtain a stronger signal; thereby increasing the signal-to-noise ratio. Accordingly, there is a trade-off between resolution in the axial direction and signal-to-noise ratio, and one can select which of these qualities is to be optimized, or the degree of trade-off between the two, for a particular application.

Figure 13:
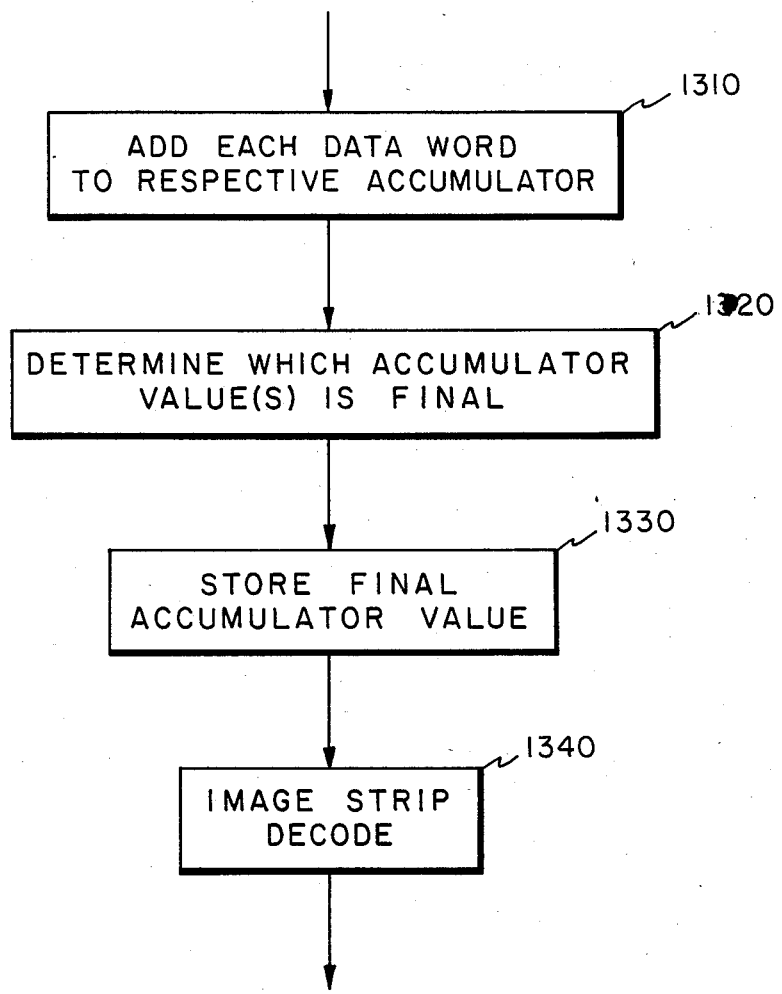
FIG. 13 is a flow diagram of the image strip decoding routine of the flow diagram of FIG. 9.

Referring to FIG. 13, there is shown a flow diagram of the routine for binning the data words from each detector, and for implementing image strip decoding (of block 1230 of FIG. 12) to obtain the desired image information. The received data word from each detector is added to a respective accumulator that is provided for each said detector (block 1310). A determination is then made (block 1320) of which accumulator value, at the present increment, represents a final accumulator value for a particular detector. (This will be a function of the number of data words being binned for a particular application. The final accumulator value(s) is then stored for each said detector (block 1330) so that a set of accumulated detector words is obtained for the larger increment over which the smaller increments are being binned. The block 1340 is then entered, this block representing image strip decoding, in the same manner as was described above in conjunction with FIG. 6 for the rotating embodiment. The decoded image strip values can then be stored, as represented by block 1240 of FIG. 12.

The invention has been described with reference to particular peferred embodiments, but variations within the spirit and scope of the invention will occur to those skilled in the art. For example, while the illustrations hereof are with respect to imaging from within a human body, it will be understood that imaging of other animate, or of inanimate bodies, can be performed. Among other possible applications are the imaging of fuel rods of an operating nuclear reactor, well logging in mineral exploration, and weld or contaminant location in pipes. In some applications the source may be located within or near the probe, and various types of detectors and aperture codes can be used.

We claim:

1. A method for imaging internal structure of a body, comprising the steps of:

introducing a radiation-emitting substance into the body;

inserting into the body a minaturized probe coupled to a cable, the probe including a plurality of radiation detectors, each detector being surrounded by a respective coded aperture, the coded apertures being at different relative rotational orientations;

receiving signals from the detectors via the cable for a series of positional translations of the probe, without rotation of the probe; and processing the signals from the detectors to obtain an image of a radiation pattern within the body.

2. The method as defined by claim 1, wherein said step of processing the signals from the detectors comprises correlating said signals with the coded aperture pattern.

3. The method as defined by claim 1, wherein said processing step comprises processing successive cylindrical image strips to obtain a cylindrical image about the axis of the probe.

4. Apparatus for imaging a radiation pattern from within a body, comprising:

a cable;

a minaturized probe coupled to the cable and insertable into the body, the probe including: a plurality of radiation detectors separated by parallel radiation-opaque axial collimators; each detector having an associated azimuthal collimator ring with a coded aperture pattern thereon, said collimator rings being disposed around their respective detectors, the coded aperture patterns of said collimator rings being at different relative rotational orientations;

means for obtaining output signals from said detectors for a series of positional translations of said probe; and means responsive to said output signals for processing said output signals to obtain an image.

5. Apparatus as defined by claim 4, wherein said azimuthal collimator rings comprise a cylinder formed of a radiation-opaque material having radiationtransparent apertures therein.

6. Apparatus as defined by claim 5, wherein the opaque regions and apertures in the cylinder are formed in a pattern of a uniformly redundant array binary code.

7. Apparatus as defined by claim 4 wherein said means for processing said output signals to obtain an image includes means for correlating said output signals with the coded aperture pattern of said collimator rings.

8. Apparatus as defined by claim 4 further comprising means for determining the position of said probe, and wherein said means for processing said output signals to obtain an image is also responsive to indications of the position of said probe.

9. Apparatus as defined by claim 8, wherein said means for determining the position of said probe comprises means for determining the length of said cable.

10. Apparatus as defined by claim 4 wherein said means for obtaining output signals from said detectors includes means for applying said output signals for transmission through said cable.

11. Apparatus as defined by claim 10 wherein said means for processing said output signals to obtain an image includes means operative to correlate said output signals with a coded aperture pattern derived from the aperture pattern of said azimuthal collimator rings.

12. Apparatus as defined by claim 11, wherein said means for processing said output signals includes means for combining delayed versions of the output signals from different ones of said radiation detectors.

13. Apparatus as defined by claim 11, wherein each of said azimuthal collimator rings has the same coded aperture pattern thereon.

14. Apparatus as defined by claim 10 wherein the number of said radiation detectors corresponds to the number of elemental rotational positions of said azimuthal collimator rings.

15. Apparatus as defined by claim 14 wherein said means for processing said output signals includes means for combining delayed versions of the output signals from different ones of said radiation detectors.

16. Apparatus as defined by claim 14 wherein each of said azimuthal collimator ring has the same coded aperture pattern thereon.

17. Apparatus as defined by claim 10 wherein each of said azimuthal collimator rings has the same coded aperture pattern thereon.

* * * * *